United States Patent [19]

Nishioka

[11] Patent Number: 4,724,481
[45] Date of Patent: Feb. 9, 1988

[54] FLAW DETECTOR FOR DETECTING FLAWS IN A SHEET

[75] Inventor: Shizuo Nishioka, Takamatsu, Japan

[73] Assignee: Futec Inc., Takamatsu, Japan

[21] Appl. No.: 939,542

[22] Filed: Dec. 8, 1986

[30] Foreign Application Priority Data

Dec. 13, 1985 [JP] Japan .................. 60-279072

[51] Int. Cl.$^4$ .................................. H04N 7/18
[52] U.S. Cl. .................. 358/106; 358/107; 250/572; 356/237
[58] Field of Search ............ 358/101, 106, 107, 282, 358/93; 250/571, 572, 578; 356/237, 239

[56] References Cited

U.S. PATENT DOCUMENTS

| | | | |
|---|---|---|---|
| 2,984,699 | 5/1961 | Dornier | 358/106 |
| 4,118,732 | 10/1978 | Ichijima et al. | 358/106 |
| 4,319,270 | 3/1982 | Kimura et al. | 358/106 |
| 4,463,373 | 7/1984 | Mikami | 358/106 |
| 4,492,477 | 1/1985 | Leser | 250/572 |
| 4,539,561 | 9/1985 | Wulff | 358/106 |
| 4,675,730 | 6/1987 | Adomaitis et al. | 358/106 |

*Primary Examiner*—Howard W. Britton
*Assistant Examiner*—John K. Peng
*Attorney, Agent, or Firm*—Brown, Martin, Haller & Meador

[57] ABSTRACT

A flaw detector, for detecting a flaw in a sheet, picks up, by means of a plurality of linear array cameras, the light of rays transmitted through a sheet. The video signals from the linear array cameras, which are appropriately processed, are used for checking whether a flaw is present or not. A sensitivity-difference correcting section corrects sensitivity differences among the cameras and among photosensitive elements of each camera, which sensitivity differences are contained in the video signal. Automatic gain control sections, for transparent and opaque flaws, respectively, control the sensitivities of the video signals. These signals are differentiated, and then compared with a predetermined slicing level, thereby to check whether transparent and opaque flaws are present or not.

30 Claims, 30 Drawing Figures

FLAW DETECTOR FOR DETECTING FLAWS IN A SHEET

BACKGROUND OF THE INVENTION

The present invention relates to a flaw detector which detects flaws which are sometimes present on the surface of a sheet or on the inner portions of a transparent sheet.

There are known sheet-flaw detection devices which photograph sheets of paper, sheet metal, or vinyl film by means of linear array cameras employing linear image sensors, i.e. CCD line sensors, each of which is composed of several hundred to several thousand photosensitive elements arranged in a linear fashion. From the video signal changes emitted from these sensors, sheet flaws such as pinholes, soiling, wrinkles, and adhering insects can be detected.

However, with these flaw detection devices, completely satisfactory flaw detection has been difficult to achieve, because problems occur in the processing of the signals, due to the different sensitivities of linear arrays, background S/N, and edge blanking. In other words, as the difference in video signals received from a portion with flaws and one without flaws becomes increasingly minute, better quality signal processing is thus required. Accordingly, a new method of flaw detection has become necessary, in order to cope with the aforementioned linear sensitivity variation, background signal S/N, and edge blanking processing problems.

SUMMARY OF THE INVENTION

Accordingly, an object of the present invention is to provide a flaw detector, for detecting flaws in a sheet, having an improved flaw-detection accuracy.

According to the present invention, there is provided a flaw detector for detecting flaws in a sheet, comprising:

- a light source for illuminating a sheet being subjected to flaw detection;
- a plurality of linear array image cameras for picking up the light rays transmitted through the sheet, and converting them into a video signal, the linear cameras being arrayed so as to cover the full width of the sheet, and each of the linear array cameras including a linear array image sensor made up of a number of photosensitive elements linearly arrayed;
- memory means corresponding to the linear array cameras, for storing the corrected sensitivity values thereof;
- correcting means corresponding to the linear array cameras, for amplifying the video signal derived from the corresponding linear array camera, at a degree of amplification corresponding to the corrected value as stored in the memory means, and for producing a sensitivity-corrected video signal;
- wave-shaping means for receiving the corrected video signal and shaping the waveform thereof, so as to clearly show a flawed portion of a sheet; and
- first flaw-check means for checking a flaw according to the shaped waveform, and for outputting the result of the check.

DETAILED DESCRIPTION OF THE PREFERRED EMBODIMENTS

An embodiment according to the present invention will now be described, with reference to the accompanying drawings.

Figure 1:
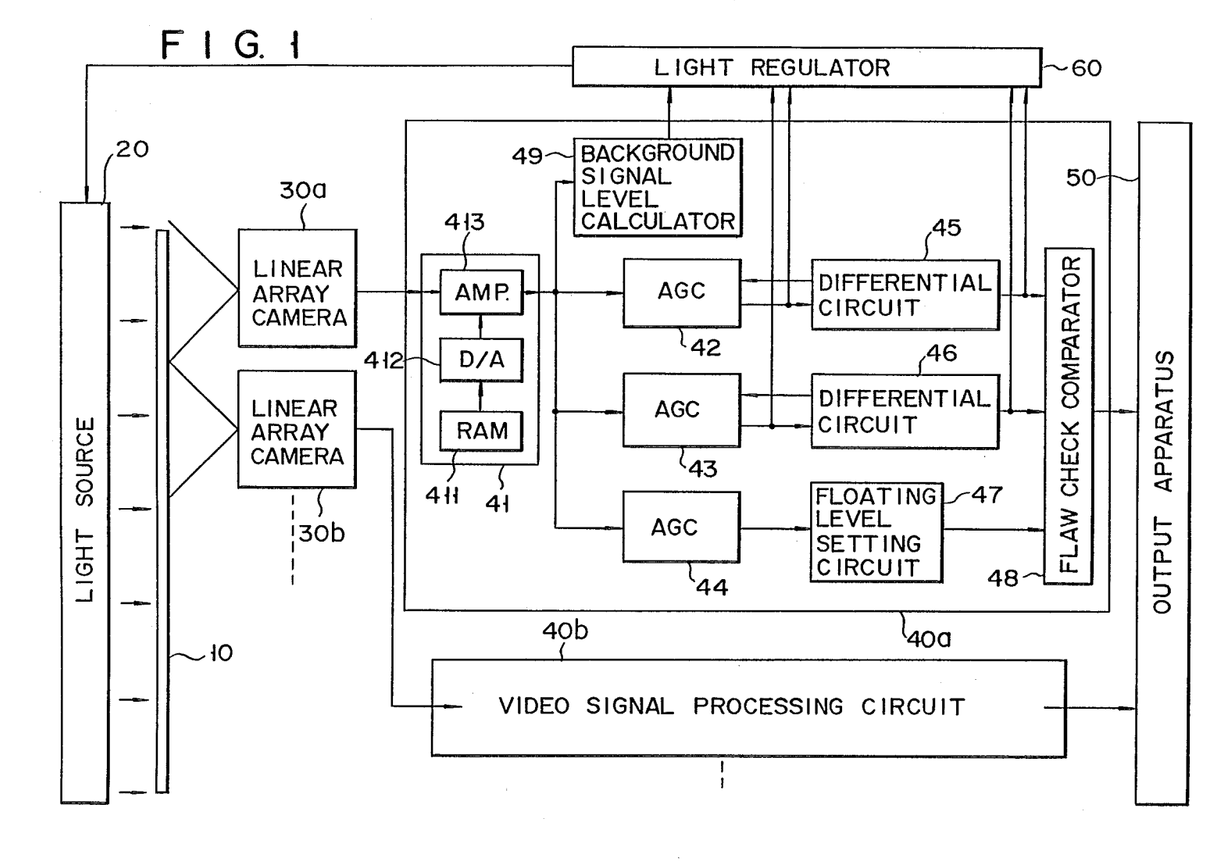
FIG. 1 is a block diagram showing a circuit configuration of a flaw detector, for detecting flaws in a sheet, according to the present invention.

FIG. 1 shows a circuit configuration of this embodiment. Tested sheet 10, which is moved in the direction perpendicular to the paper plane, is illuminated by light source 20. Tested sheet 10 is picked up by linear array cameras 30, such as cameras 30a, 30b . . . from the side opposite to light source 20. The number of cameras 30 used is sufficient to photograph the full width of tested sheet 10. Video signals from cameras 30 are supplied to video signal-processing circuit 40, such as processing circuits 40a, 40b . . . Video signal-processing circuits check whether flaws are present or not, and the results are output to output apparatus 50, such as a display device and a printing device.

Each video signal-processing circuit 40 comprises sensitivity difference-correcting section 41, transparent-flaw automatic gain control (AGC) section 42, opaque-flaw AGC section 43, AGC section 44 for slicing-with-floating level process, transparent-flaw differential circuit 45, opaque-flaw differential circuit 46, floating level-setting circuit 47, flaw-check comparator section 48, and background-level calculator section 49.

Figure 2A:
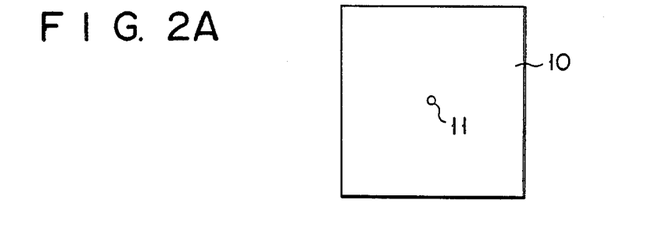
FIGS. 2A and 3A are views illustrating examples of sheets having different flaws.
Figure 2B:
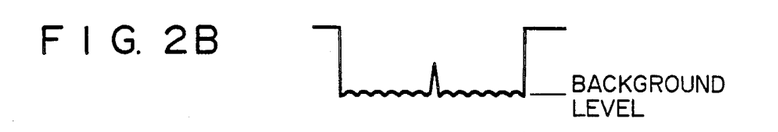
FIGS. 2B and 3B show waveforms of video signals obtained when the sheets shown in FIGS. 2A and 3A are photographed.

The term "transparent flaw" means a typical flaw in a sheet, such as a hole. Specifically, when pinhole 11 is present in sheet 10, as is shown in FIG. 2A, and sheet 10 is scanned by one of the linear array cameras, a video signal is obtained, whose level depends on the amount of transmitted light, as is shown in FIG. 2B. A flaw whose signal level is higher than the background signal level of the video signal, is referred to as a "transparent flaw".

Figure 3A:
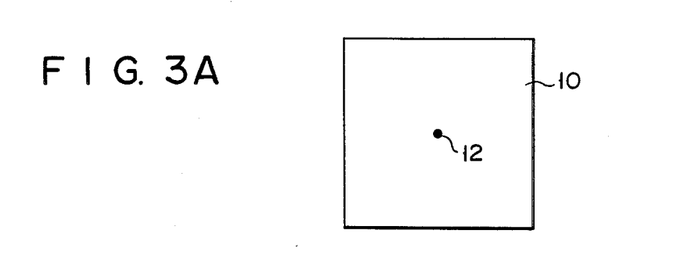
Figure 3B:
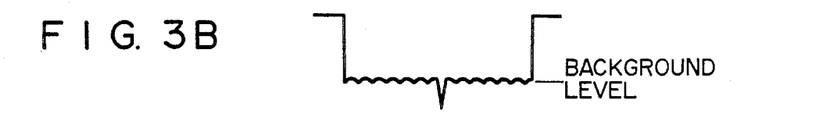

The term "opaque flaw" means a typical flaw in a sheet, such as a black spot. Specifically, when black spot 12 is present in sheet 10, as is shown in FIG. 3A, and sheet 10 is scanned by one of the linear array cameras, a video signal is obtained, whose level depends on the amount of transmitted light, as is shown in FIG. 3B. A flaw whose signal level is lower than the background signal level of the video signal, is referred to as an "opaque flaw".

In video signal-processing unit 40a, the sensitivity difference of the supplied video signal is first corrected by sensitivity difference correcting section 41. Specifically, in section 41, the sensitivity difference among cameras 30 and that among the photosensitive elements of corresponding to camera 30 are corrected, since these differences result in the difference in levels among the video signals, which, in the later step, will cause errors in the signal-processing circuit.

As is shown in FIG. 1, sensitivity difference-correcting section 41 comprises ROM table 411, digital/analog (A/D) converter 412, and amplifier 413. ROM table 411 stores the corrected values for the sensitivity difference among cameras and/or the corrected values for the sensitivity difference of each photosensitive element of that camera. The correcting values are read out by the address circuit (not shown). Digital/analog (A/D) converter 412 converts into analog values the corrected values which are read out from ROM table 411. Amplifier 413 controls its degree of amplification in accordance with the analog-converted corrected values.

The video signal whose sensitivity difference is corrected by sensitivity difference-correcting section 41, is differentiated and then compared, by the comparator, with a predetermined slicing level, and it is checked whether flaws are present or not. The reason why the video signal is differentiated will be given below.

Figure 2C:
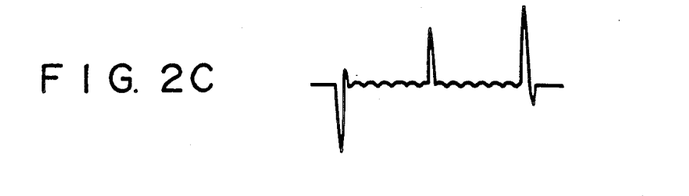
FIGS. 2C and 3C show waveforms of differentiated video signals of FIGS. 2B and 3B.
Figure 3C:
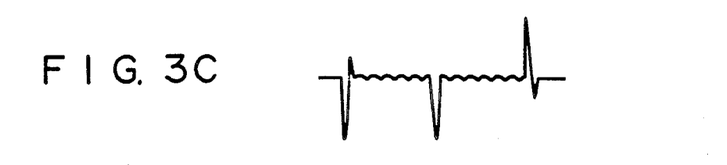

The waveform of the differential signal shows the presence of a flaw more clearly than that of the video signal. For example, if the video signals shown in FIGS. 2B and 3B are differentiated, the differential signals are as shown in FIGS. 2C and 3C. The differential waveform contains pulsative waveforms at the leading and trailing edges of the video signal. These pulsative waveforms can be discriminated from the flaw, by an edge-masking technique to be described later. Therefore, these pulsative waveforms will be ignored in the subsequent description.

Figure 4:
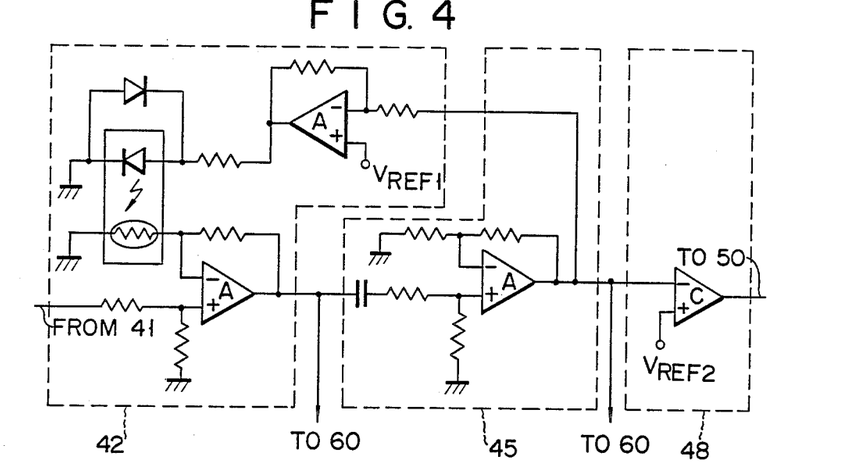
FIG. 4 is a circuit diagram illustrating a circuit for checking flaws, based on the peak values of the differentiated wave.

Actually, the corrected video signal is supplied to both transparent-flaw AGC section 42 and opaque-flaw AGC section 43. The signals which are sensitivity-controlled by these units, are respectively supplied to differential circuits 45 and 46. Transparent-flaw AGC section 42 and opaque-flaw AGC section 43 control the sensitivity of the video signals, in accordance with the outputs of differential circuits 45 and 46. The differential outputs of respective differential circuits 45 and 46 are supplied to flaw-check comparator section 48, and are compared with the predetermined slicing levels. An example of an actual circuit configuration containing transparent-flaw AGC section 42, transparent-flaw AGC differential circuit 45, and the transparent flaw-check comparator of transparent-check comparator section 48 is shown in FIG. 4. The circuits for the opaque flaw detection process can be configured in the same manner.

In FIG. 4, "A" designates an operational amplifier, "C" a comparator, "$V_{REF1}$" a predetermined reference potential, and "$V_{REF2}$" a reference potential used for setting the slicing level.

The reason why separate AGCs, one for transparent flaws, and the other for opaque flaws, are provided, will be described below.

Figure 5A:
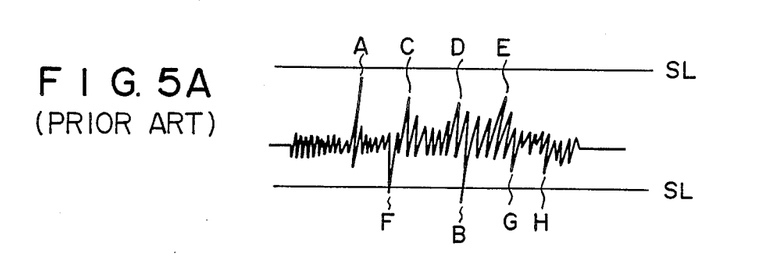
FIG. 5A shows a differentiated waveform and slicing levels when a conventional automatic gain control is used for automatic gain controlling.
Figure 5B:
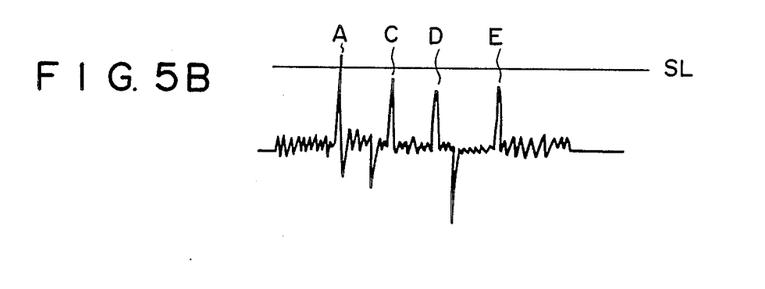
FIGS. 5B and 5C show differentiated waveforms and slicing levels when separate automatic gain controls are used for detecting transparent flaws and opaque flaws according to this invention.
Figure 5C:
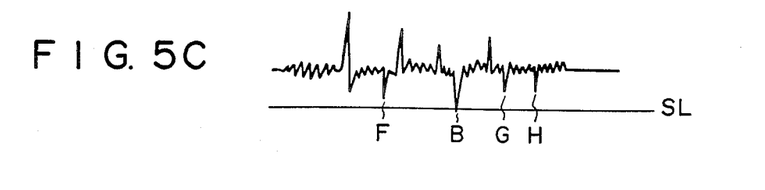

The differential signal peak value of a transparent flaw and that of an opaque flaw are different, and therefore, if a single AGC is employed, it is difficult to set the levels of the comparator for subsequent flaw checking. It is this difficulty which has been the major cause of errors arising in the detection of flaws. As is shown in FIG. 5A, in the case where a single AGC is used, there is only a slight difference between the peak values (indicated by characters A and B) corresponding to the flaw to be detected, and the peak values (indicated by C through H) not corresponding to the flaw. Accordingly, even if the slicing level (SL) is appropriately set for both transparent-flaw and opaque-flaw comparators, the case often arises in which the flaw (peak value A) is not detected and peak value F is mistakenly detected. By providing separate AGCs for transparent flaws and for opaque flaws, the accuracy of flaw detection can be improved. Specifically, by increasing the degree of amplification in the transparent-flaw AGC, and decreasing it in the opaque-flaw AGC, only transparent-flaws and opaque-flaws (peak values A and B) can be detected, as is shown in FIGS. 5B and 5C.

Figure 6A:
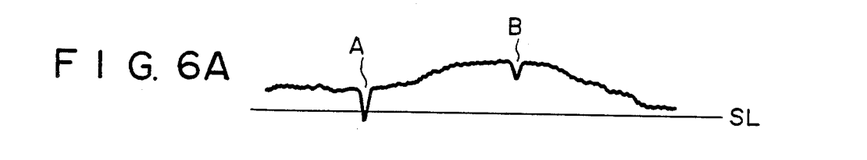
FIGS. 6A to 6D show a set of waveforms for explaining process used for checking flaws, based on a slicing-with-floating level of the video signal.
Figure 6B:
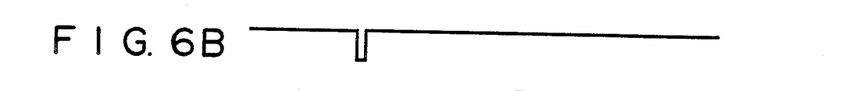
Figure 6C:
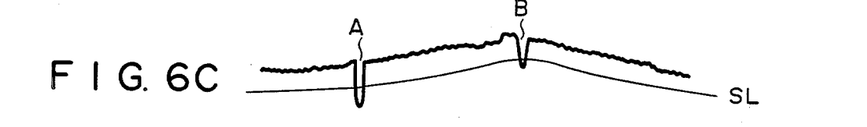
Figure 6D:
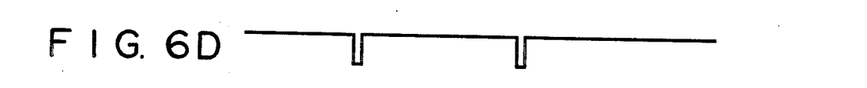

The video signal whose sensitivity difference is corrected by sensitivity difference-correction section 41, is sensitivity-controlled by floating-level AGC section 44, and is used for setting the floating level in floating level-setting circuit 47. The floating level and the above video signal are supplied to flaw-check comparator section 48 and compared, and it is checked whether flaws are present or not. Specifically, if a variation in the background signal level contained in the video signal is great, then a flaw exists which cannot be detected, by the flaw check process, on the basis of the above peak value of the differential waveform. To detect such a flaw, the video signal is used. In this case, however, as is shown in FIG. 6A, if the video signal having a great variation in background signal levels is simply compared with a predetermined slicing level (SL), then the flaw (peak value B) shown in FIG. 6B cannot be detected. To avoid this, comparison is made with the floating level, (i.e., SL), which changes according to the background signal level, as is shown in FIG. 6C. In this way, the flaws (peak values A and B) are detected, as shown in FIG. 6D.

Figure 7:
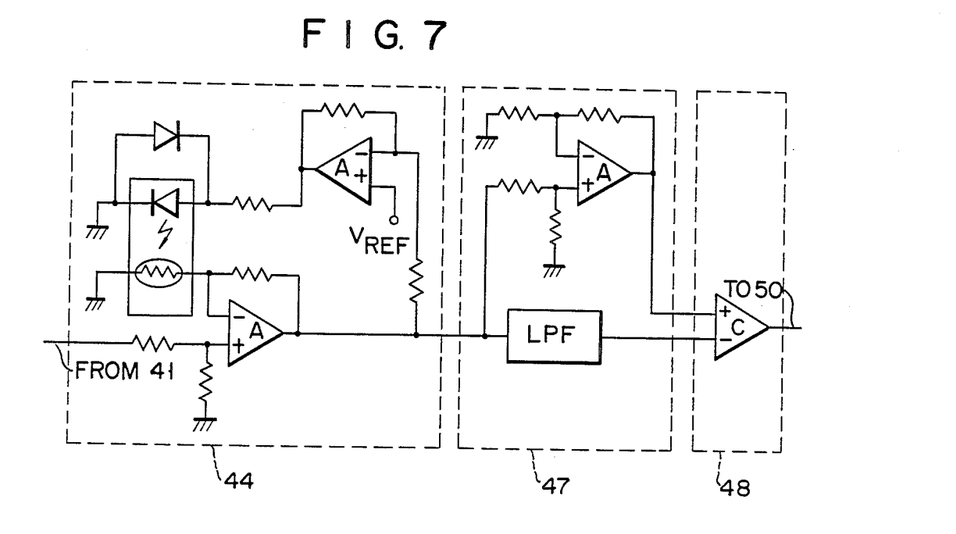
FIG. 7 is a circuit diagram illustrating a circuit for checking flaws on the basis of the slicing-with-floating level of the video signal.

FIG. 7 shows an example of the actual circuit configuration of floating-level AGC section 44, floating level-setting circuit 47, and flaw-check comparator 48. In FIG. 7, "A" designates an operational amplifier, "C" a comparator, and "$V_{REF}$" a predetermined reference potential.

Figure 8A:
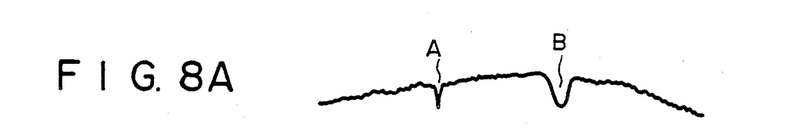
FIGS. 8A to 8F show a set of waveforms for explaining the flaw check process based on the slicing-with-floating level and the peak value of differential wave.
Figure 8B:
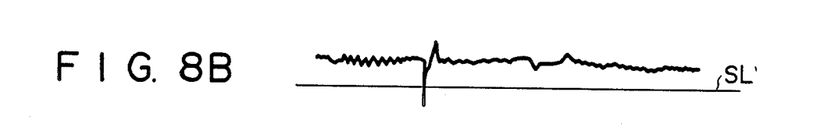
Figure 8C:
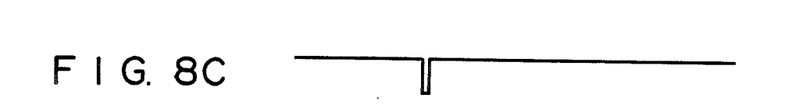
Figure 8D:
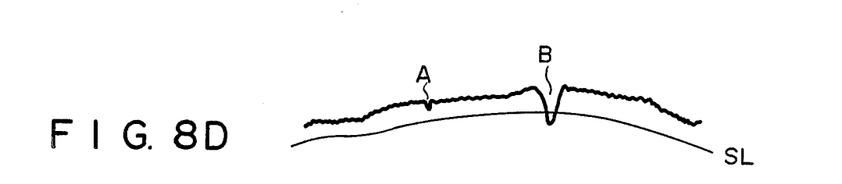
Figure 8E:
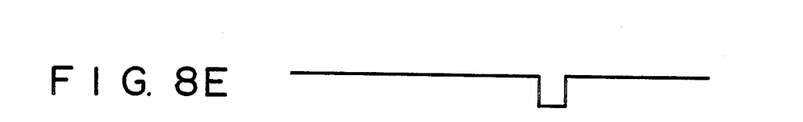
Figure 8F:
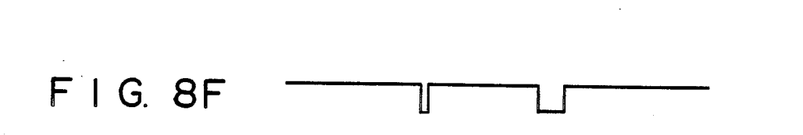

When the flaw check based on the peak value of the differential waveform and that based on the floating level of the video signal are both used, flaws having low flaw S/N can be detected more reliably than when only the flaw check based on the peak value is used. Specifically, if a video signal having a large variation background signal level, (as is shown in FIG. 8A), and also having peak values A and B corresponding to flaws, is compared with the slicing level (SL), after being differentiated, (as is shown in FIG. 8B), then a flaw exists (peak value B) which cannot be detected, as is shown in FIG. 8C. If SL is changed according to the background level, as is shown in FIG. 8D for comparison, the flaw can be detected, as is shown in FIG. 8E. Accordingly, using these flaw-check methods together enables the detection of a flaw which cannot be detected using either single method.

Video signal-processing circuit 40a includes background signal-level calculator section 49. The present flaw detector determines that the video signal whose level differs greatly from the background signal level represents the presence of a flaw. It is preferable, therefore, for the background signal level to be almost constant. However, tested sheet 10 has an irregularity in light transmissivity which results in a background signal-level variation. It is necessary, therefore, that the amount of light emitted by light source 20 is regulated so as to keep the background signal level almost constant. To this end, it is important to calculate the background signal level.

Figure 9:
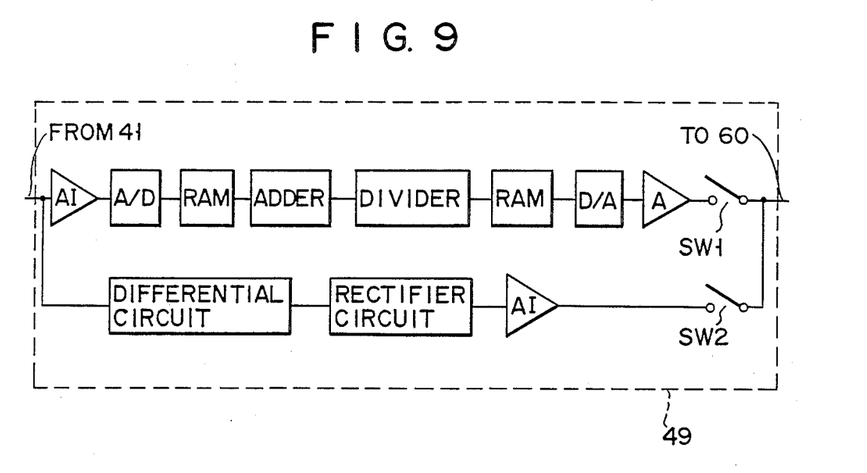
FIG. 9 is a block diagram of a circuit configuration of a background signal-level calculator.

FIG. 9 shows the circuit configuration of an example of background signal-level calculator section 49. In this figure, "AI" designates an integration amplifier, and "A" an amplifier (or an operational amplifier). This circuit calculates the mean value of a plurality of video signals derived from linear array camera and also the mean value of the amplitudes of the video signals. The mean value of the video signals can be obtained by adding together the integration waveforms of a plurality of video signals and dividing the sum by the number of additions performed. The mean value of the amplitudes is obtained by full-wave rectifying the differential waveforms of the video signals. By using select switches SW1 and SW2, the mean value of the same signals and/or the amplitude mean value are supplied to light regulator 60 which regulates the amount of light from light source 20.

The amount of light emitted by light source 20 is almost constant for the same sheet 10, though it varies slightly due to the correction of the variation in the background signal level. However, if there is a change in the weight per one square meter (hereinafter referred to as the area weight) of tested sheet 10, for example, the video signal level changes greatly. In order that the flaw detector be able to maintain a constant flaw-detection ability, it is preferable that the video signal level be kept fixed, even if the area weight of the tested sheet varies. To realize this, the flaw detector of the present invention uses light-regulator 60 which regulates the amount of light emitted by light source 20, by using the levels of transparent-flaw signals and opaque-flaw signals derived from the AGC sections and the differential transparent- and opaque-flaw signals.

Figure 10:
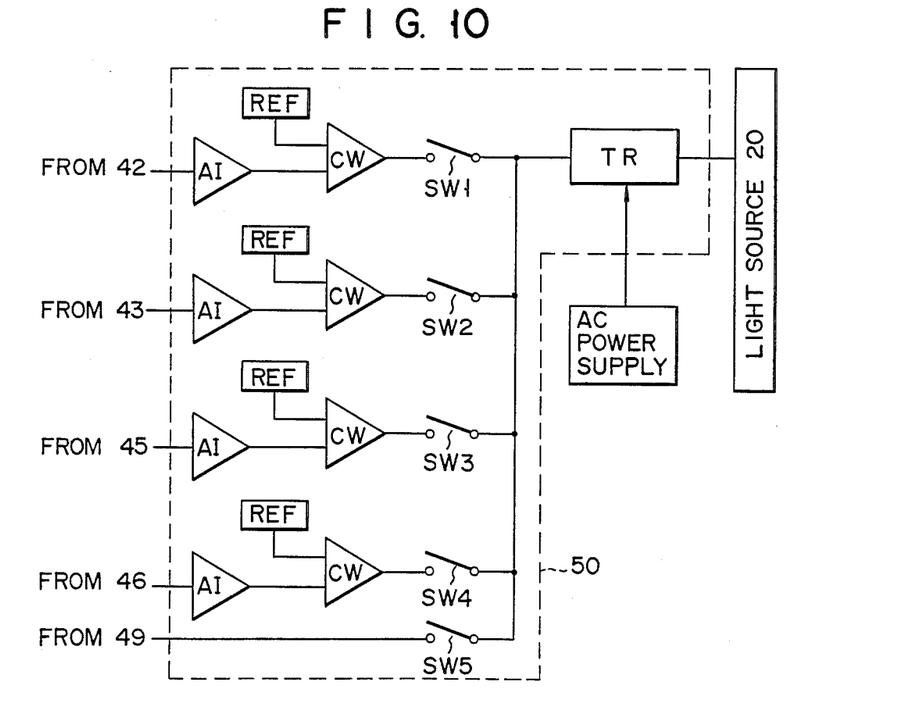
FIG. 10 is a block diagram of a circuit configuration of a light-regulator circuit.

FIG. 10 is a block diagram showing an example of the circuit configuration of this type of light-regulator 60.

In this circuit 60, transparent-flaw and opaque-flaw AGC levels and differential signals are supplied from transparent-flaw AGC section 42, opaque-flaw AGC section 43, transparent-flaw differential circuit 45, and opaque-flaw differential circuit 46. The mean value of video signals and the amplitude mean value for correcting the background signal-level variation, are supplied by background signal-level calculator 49. In the figure, "AI" means integration amplifier, "CW" window comparator, "REF" indicates a level-setting device, and "TR" triac driver and triac. The level-setting device sets the upper and lower levels of the window comparator. When the signal from the integration amplifier is between these upper and lower levels, the output of the window comparator is "0". When the signal from the integration amplifier is above the upper level, the output is "high", and when lower than the lower level, the output level is "low". The output of the window comparator, which depends on the signals from transparent-flaw AGC section 42, opaque-flaw AGC section 43, transparent-flaw differential circuit 45, and opaque-flaw differential circuit 46, and further, the output of background signal-level calculator 49, are applied to the triac driver and triac, either separately or in combined form, by means of selector switches SW1 to SW5. These signals control the amount of light emitted by light source 20. Thus, when sheet 10 has an area weight of between 50 g and 180 g, no adjustment is required to compensate for the background signal-level variation.

The leading and trailing edges of the video signal at the width edges of tested sheet 10, i.e., the edge signals, serve as false signals for flaw detection. To prevent this, these edge signals are masked by placing opaque masking plates on the inner sides of the edges of tested sheet 10. When the width of tested sheet 10 is different, the position of each masking plate must be adjusted so that each side of tested sheet 10 may be masked with one of the masking plates by 10 through 30 mm from each side of tested sheet 10. In other words, the mask adjustment requires time and effort, and flaws near the edges of tested sheet 10 cannot be detected.

Figure 11A:
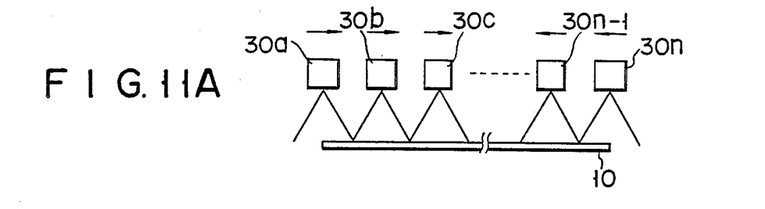
FIGS. 11A to 11E show views for explaining an edge-masking process.
Figure 11B:
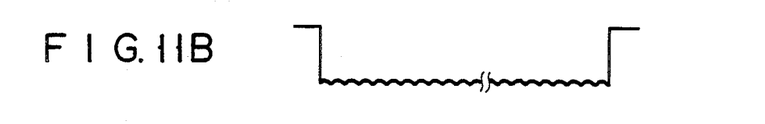
Figure 11C:
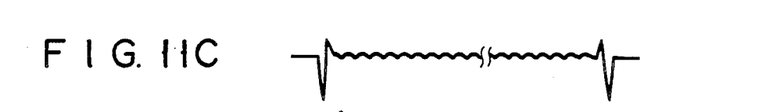
Figure 11D:
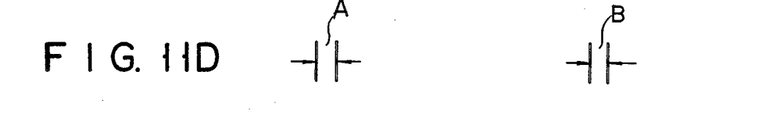
Figure 11E:
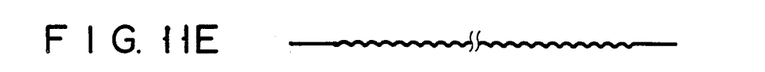

To solve such a problem, an approach was proposed in which the edge masking is executed at the trailing edge of tested sheet 10. As is shown in FIG. 11B, if tested sheet 10, which moves in a direction perpendicular to the plane of this drawing, is photographed by "n" of the linear array cameras (30a, 30b, ... 30n), a video signal like that shown in FIG. 11A is obtained. In this case, the scanning direction of the cameras, as is shown by the arrows in FIG. 11A, is set from the outside of tested sheet 10, toward the inner side. When this signal is differentiated, a high signal level is generated at the width edge of detected sheet 10, or the trailing edge of the video signal. This high signal level is mistaken for a signal level indicative of a flaw. As is shown in FIG. 11D, after the trailing edge of the video signal has been detected, the signals from a specified number of photosensitive elements (for example 15) are placed within the ineffective areas (shown by A and B in the figure). In other words, a specified number "n" of photosensitive elements, from among those which detected the signals corresponding to the trailing edge of the video signals, are rendered ineffective, and a differential signal as shown in FIG. 11E, is obtained.

Figure 12:
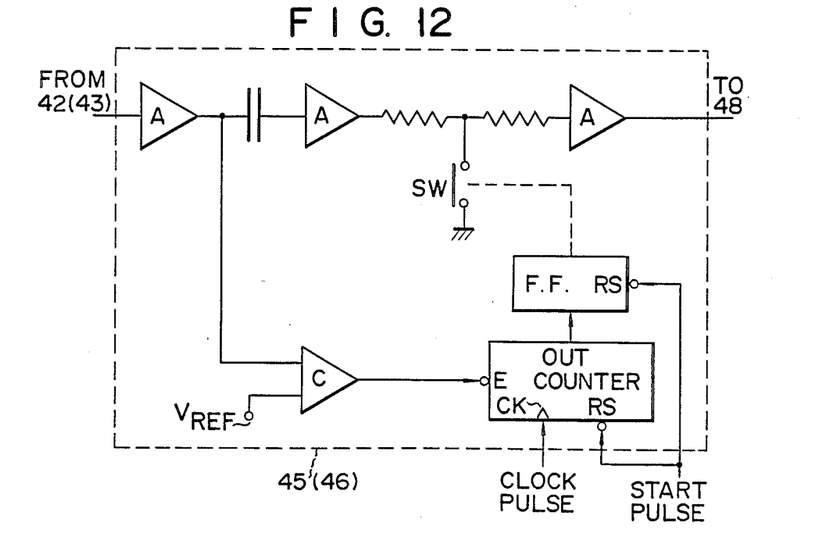
FIG. 12 is a circuit diagram of a differential circuit which is modified so as to execute the edge masking.

This kind of edge masking can be obtained by the use of differential circuits, for example, differential circuits 45 and 46 as configured shown in FIG. 12. In this figure, "A" stands for an operational amplifier, and "C" stands for a comparator. "FF" designates a flip-flop and "SW" an analogue switch. Analog switch "SW" is turned ON and OFF according to the output from flip-flop "FF". When the trailing edge of the video signal is detected by the comparator, the counter starts to count. When a number of clock signals equal to the specified number of photosensitive elements to be masked has been counted, the counter generates a pulse. This pulse is latched by the flip flop, and the switch is opened. This causes a differential signal to be output to comparator section 48.

What is claimed is:

1. A flaw detector for detecting flaws in a sheet, comprising:
   a light source for illuminating a sheet being subjected to flaw detection;
   a plurality of linear array image cameras for picking up the light rays transmitted through said sheet, and converting them into a video signal, said linear cameras being arrayed so as to cover the full width of said sheet, and each of said linear array cameras including a linear array image sensor made up of a number of photosensitive elements linearly arrayed;
   memory means corresponding to said linear array cameras, for storing the corrected sensitivity values thereof;
   correcting means corresponding to said linear array cameras, for amplifying the video signal derived from the corresponding linear array camera, at a degree of amplification corresponding to the corrected value as stored in said memory means, and for producing a sensitivity-corrected video signal;
   wave-shaping means for receiving said corrected video signal and shaping the waveform thereof, so as to clearly show a flawed portion of a sheet; and
   first flaw-check means for checking a flaw according to the shaped waveform, and for outputting the result of said check.

2. The flaw detector according to claim 1, wherein the corrected sensitivity value of each of said linear array cameras, which is stored in said memory means, comprises a sensitivity value of each of said photosensitive elements in the corresponding linear array camera.

3. The flaw detector according to claim 1, wherein said first flaw-check means includes two flaw-detecting means, one each for transparent flaws and opaque flaws, said transparent flaw-check means checks a transparent flaw, whose signal level is higher than the background signal level of said video signal, and said opaque flaw-check means checks an opaque flaw, whose signal level is lower than the background signal level of said video signal.

4. The flaw detector according to claim 3, wherein said wave-shaping operation is performed to differentiate the corrected video signal so as to have a differential waveform.

5. The flaw detector according to claim 4, wherein said transparent flaw-check means determines that a flaw is present when said differential waveform has a higher level than a predetermined slicing level, and said opaque flaw-check means determines that a flaw is present when said differential waveform has a lower level than a predetermined slicing level.

6. The flaw detector according to claim 5, wherein said transparent and opaque flaw-check means, respectively, include automatic gain control (AGC) means for transparent and opaque video signals, which are for automatically controlling sensitivities according to said differential waveform.

7. The flaw detector according to claim 6, wherein said AGC means for transparent flaws amplifies said corrected signal.

8. The flaw detector according to claim 6, wherein said AGC means for opaque flaws attenuates said corrected signal.

9. The flaw detector according to claim 6, wherein said flaw detector further includes light-regulating means for regulating the amount of illuminating light from said light source, according to said differential waves and said automatically sensitivity-controlled video signals from said transparent and opaque flaw-check means.

10. The flaw detector according to claim 1, further comprising second flaw-check means for comparing said corrected video signal as received and a slicing level which changes according to the background signal level of said received corrected video signal, and for outputting the result of the comparison.

11. The flaw detector according to claim 1, further comprising background signal-level calculating means for receiving said corrected video signal and calculating a background signal level thereof, and light-regulating means for regulating the amount of illuminating light from said light source, according to the calculated background signal level.

12. The flaw detector according to claim 11, wherein said background signal-level calculating means supplies to said light-regulating means one of the mean value of video signals, as obtained through the scannings performed by said linear array cameras, and the mean value of the amplitudes of said video signals, as the calculated background signal level.

13. The flaw detector according to claim 11, wherein said background signal-level calculating means supplies to said light-regulating means the mean value of video signals, as obtained through the scannings by means of said linear array cameras, and the mean value of the amplitudes of said video signals, as the calculated background signal level.

14. The flaw detector according to claim 1, further comprising means for masking the negative going pulsative waveforms of said video signal, which represent the width edges of said sheet.

15. The flaw detector according to claim 14, wherein said edge masking means performs the edge masking in a manner that after the trailing edge of said video signal is detected, the supply of the waveform signal from said wave shaping means to said first flaw-check means during a predetermined period, is made invalid.

16. A flaw-detecting method for detecting flaws in a sheet, comprising the steps of:
   illuminating a sheet to be flaw-detected, by use of a light source;
   picking up the light rays transmitted through said sheet by a plurality of linear cameras being arrayed so as to cover the full width of said sheet, each of said linear array cameras including a linear array image sensor made up of a number of photosensitive elements linearly arrayed, and further producing a video signal corresponding to the amount of transmitted light;
   amplifying the video signal, derived from the corresponding linear array cameras, at a degree of amplification corresponding to the corrected value, as stored in memory means corresponding to said linear array cameras, thereby to obtain a sensitivity-corrected video signal;
   shaping the waveform of said corrected video signal, by said waveform-shaping means, so as to clearly show a flawed portion of a sheet; and
   checking a flaw, according to the shaped waveform, by first flaw-check means.

17. The method according to claim 16, wherein the corrected sensitivity value of each of said linear array cameras, which is stored in said memory means, comprises a sensitivity value of each of said photo-sensing elements in the corresponding linear array camera.

18. The method according to claim 16, wherein said first flaw-check means includes two flaw-detecting means, one each for transparent flaws and opaque flaws, said transparent flaw-check means checks a transparent flaw, whose signal level is higher than the background signal level of said video signal, and said opaque flaw-check means checks an opaque flaw, whose signal level is lower than the background signal level of said video signal.

19. The method according to claim 18, wherein said wave-shaping operation is performed to differentiate the corrected video signal so as to have a differential waveform.

20. The method according to claim 19, wherein said transparent flaw-check means determines that a flaw is present when said differential waveform has a higher level than a predetermined slicing level, and said opaque flaw-check means determines that a flaw is present when said differential waveform has a lower level than a predetermined slicing level.

21. The method according to claim 20, wherein said transparent and opaque flaw-check means, respectively, include automatic gain control (AGC) means for transparent and opaque video signals, which are for automatically controlling sensitivities according to said differential waveform.

22. The method according to claim 21, wherein said AGC means for transparent flaws amplifies said corrected signal.

23. The method according to claim 21, wherein said AGC means for dark flaws attenuates said corrected signal.

24. The method according to claim 21, further comprising the step of regulating the amount of illuminating light from said light source, according to said differential waves and said automatically sensitivity controlled video signals from said transparent and opaque flaw check means, by a light regulating means.

25. The method according to claim 16, further comprising the step of comparing said corrected video signal as received and a slicing level which changes according to the background signal level of said received corrected video signal, and for outputting the result of the comparison.

26. The method according to claim 16, further comprising the steps of receiving said corrected video signal and calculating a background signal level thereof by a background signal-level calculating means, and regulating an amount of illuminating light from said light source, according to the calculated background signal level, by a light-regulating means.

27. The method according to claim 26, wherein said background signal-level calculating means supplies to said light-regulating means one of the mean value of video signals, as obtained through the scannings by means of said linear array cameras, and the mean value of the amplitudes of said video signals, as the calculated background signal level.

28. The method according to claim 26, wherein said background signal-level calculating means supplies to said light-regulating means the mean value of video signals, as obtained through the scannings by means of said linear array cameras, and the mean value of the amplitudes of said video signals, as the calculated background signal level.

29. The method according to claim 16, further comprising the step of edge masking the negative going pulsative waveforms of said video signal, which represent the width edges of said sheet.

30. The method according to claim 29, wherein said edge masking step performs the edge masking in a manner that after the trailing edge of said video signal is detected, the supply of the waveform signal from said wave-shaping means to said first flaw check means during a predetermined period, is made invalid.

* * * * *